United States Patent [19]

Brooks et al.

[11] Patent Number: 4,996,151
[45] Date of Patent: Feb. 26, 1991

[54] METHOD FOR PRODUCING THE EAG I RESTRICTION ENDONUCLEASE AND METHYLASE

[75] Inventors: Joan E. Brooks; Laura A. Sznyter, both of Beverly, Mass.

[73] Assignee: New England Biolabs, Inc., Beverly, Mass.

[21] Appl. No.: 195,882

[22] Filed: May 19, 1988

[51] Int. Cl.$^5$ .................. C12N 15/54; C12N 75/55; C12N 1/20
[52] U.S. Cl. .................. 435/172.3; 435/199; 435/252.3; 435/320.1; 435/193; 435/252.33; 536/27; 935/29; 935/73; 935/80; 935/82
[58] Field of Search .................. 435/172.3, 193, 199, 435/320, 252.3, 252.33; 935/29, 73, 80, 82; 536/27

[56] References Cited

U.S. PATENT DOCUMENTS 6.707,079  7/1988  Wilson .

FOREIGN PATENT DOCUMENTS 0193413  9/1986  European Pat. Off. .

OTHER PUBLICATIONS

Chandrasegaran, S. et al., (1987) Structure and Expression, vol. I, Sarma et al. (eds.), Adenine Press, 149–156.
Brooks, J. E. (1987) Met. Enz., vol. 152, 113–129.
Sohail, A. et al. (1987) Pakistan J. Zool. 19(4), 371–391.
Kaue, L. et al. (1986) Acta Microbiologica Polonica 35(3/4), 317–320.
Mann et al., Gene 3: 97–112, 1978.
Kosysh et al., Molec. Gen. Genet. 178: 717–719, 1980.
Walder et al., Proc. Nat. Acad. Sci. U.S.A. 78: 1503–1507, 1981.
Bougueleret et al., Nucleic Acids Res. 12: 3659–3676, 1984.
Gingeras & Brooks, Proc. Natl. Acad. Sci. U.S.A. 80: 402–406, 1983.
Theriault & Roy, Gene 19: 355–359, 1982.
Blumenthal et al., J. Bacteriol. 164: 501–509, 1985.
Kiss et al., Nucleic Acids Res. 13: 6403–6421, 1985.
Szomolanyi et al., Gene 10: 219–225, 1980.
Janulaitis et al., Gene 20: 197–204, 1982.
Kiss & Baldauf, Gene 21: 111–119, 1983.
Walder et al., J. Biol. Chem. 258: 1235–1241, 1983.
Raleigh & Wilson, Proc. Natl. Acad. Sci., U.S.A. 83: 9070–9074, 1986.
Maniatis et al., Molecular Cloning; A Laboratory Manual; Cold Spring Harbor Laboratories, New York; pp. 368–369, 1982.
Greene, P. J. et al. (1981) J. Biol. Chem., 256 (5), 2143–2153.
Newman, A. K. et al. (1981) J. Biol. Chem., 256(5), 2131–2139.
Schoner, B. et al. (1983) Gene 24, 227–238.
Walder, R. Y. et al. (1984) J. Biol. Chem., 259(12), 8015–8026.
Kauc, L. et al. (1987) Chem Abst. 107: 19790g.
Sohail, A. et al. (1989) Chem. Abst. 111: 35574c.
Butkus, V. V. et al. (1985) Chem. Abst. 103: 137590g.
Kessler, C. et al. (1985) Gene 33, 1, 22, 97, 98.
Wilson, G. C. (1988) Trends in Genetics 4(11), 314–318.
Lunnen, K. P. et al. (1988) Gene 24, 25–32.
Borck, K. et al. (1976) Molec. Gen. Genet. 146, 199–207.
Roberts, R. J. (1989) Nuc. Acids Res. 17 (Suppl.), 1347–1387.

Primary Examiner—Elizabeth C. Weimar
Assistant Examiner—Charles L. Patterson
Attorney, Agent, or Firm—Gregory D. Williams; David G. Conlin

[57] ABSTRACT

The present invention is directed to a method for cloning and producing the Eag I restriction endonuclease by (1) introducing the restriction endonuclease gene from E. agglomerans ATCC into a host whereby the restriction gene is expressed; (2) fermenting the host which contains the vector encoding and expressing the Eag I restriction endonuclease, and (3) purifying the Eag I restriction endonuclease from the fermented host which contains the vector encoding and expressing the Eag I restriction endonuclease activity.

10 Claims, 8 Drawing Sheets

VECTOR CONSTRUCTED FOR EagI CLONING

Mapping Gel of pEagRM2.9-19b

A. Sac I digest
B. Sac I and Ava I digest
C. Sac I and Cla I digest
D. Sac I and Sty I digest
E. λ-Bst EII and pBR322-Msp I standards
F. Sac I and Eco RV digest
G. Sac I and Bsu 36I digest
H. Eco RV and Sty I digest
I. Dra I digest
J. φX-Hae III and pBR322-Msp I standards
K. Dra I and Sty I digest
L. Dra I and Ava I digest
M. Dra I and Sac I digest Run on a 1.5% Tris-Borate Agarose gel

FIG. 3D

Titres of Crude Extract From pEagRM2.9, pEagRM2.9-19a and pEagRM2.9-19b

A B C D E F G H I J K L M N O P

Digestion of pBR322 linearized at the Pst I site:
A. λ-Bst EII standard
B. 1u/μl of pEagRM2.9
C. 5u/μl of pEagRM2.9
D. 25u/μl of pEagRM2.9
E. 125u/μl of pEagRM2.9
F. 625u/μl of pEagRM2.9
G. 1u/μl of pEagRM2.9-19a
H. 5u/μl of pEagRM2.9-19a
I. 25u/μl of pEagRM2.9-19a
J. 125u/μl of pEagRM2.9-19a
K. 625u/μl of pEagRM2.9-19a
L. 1u/μl of pEagRM2.9-19b
M. 5u/μl of pEagRM2.9-19b
N. 25u/μl of pEagRM2.9-19b
O. 125u/μl of pEagRM2.9-19b
P. 625u/μl of pEagRM2.9-19b Note: pEagRM2.9 is complete between 5 and 25u/μl; pEagRM2.9-19b complete between 25 and 125u/μl; and pEagRM2.9-19a is complete at ~125u/μl.

FIG. 4

METHOD FOR PRODUCING THE EAG I RESTRICTION ENDONUCLEASE AND METHYLASE

BACKGROUND OF THE INVENTION

The present invention relates to clones for the Eag I restriction endonuclease and modification methylase, and to the production of these enzymes from the clones.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Over one hundred different restriction endonucleases have been identified among many hundreds of bacterial species that have been examined to date.

Bacteria usually possess only a small number restriction endonucleases per species. The endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences (AT)GGCC(AT), PuGCGCPy and GGCC respectively. *Escherichia coli* RY13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecules and cleaving them each time that the recognition sequence occurs. The disintegration that results inactivates many of the infecting genes and renders the DNA susceptible to further degradation by exonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries' i.e. populations of clones derived by 'shotgun' procedures, when they occur at frequencies as low as $10^{-3}$ to $10^{-4}$. Preferably, the method should be selective, such that the unwanted, majority, of clones are destroyed while the desirable, rare, clones survive.

Type II restriction-modification systems are being cloned with increasing frequency. The first cloned systems used bacteriophage infection as a means of identifying or selecting restriction endonuclease clones (HhaII: Mann et al., Gene 3: 97–112, (1978); EcoRII: Kosykh et al., Molec. gen. Genet 178: 717–719, (1980); PstI: Walder et al., Proc. Nat. Acad. Sci. USA 78 1503–1507, (1981)). Since the presence of restriction-modification systems in bacteria enables them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E.coli* cloning plasmids (EcoRV: Bougueleret et al., *Nucleic Acids Res.* 12:3659–3676, (1984); PaeR7: Gingeras and Brooks, Proc. Natl. Acad. Sci. SA 80:402–406, (1983); Theriault and Roy, Gene 19:355–359, (1982); PvuII: Blumenthal et al., *J.Bacteriol.* 164:501–509, (1985)).

A third approach, and one that is being used to clone a growing number of systems, involves selecting for an active methylase gene referring to our patent application No. 707079 and (BsuRI: Kiss et al., *Nucleic Acids Res.* 13:6403–6421, (1985)). Since restriction and modification genes tend to be closely linked, clones containing both genes can often be isolated by selecting for just the one gene. Selection for methylation activity does not always yield a complete restriction-modification system however, but instead sometimes yields only the methylase gene (BspRI: Szomolanyi et al., Gene 10:219–225, (1980); BcnI: Janulaitis et al, Gene 20: 197–204 (1982); BsuRI: Kiss and Baldauf, Gene 21: 111–119, (1983); and MspI: Walder et al., *J. Biol. Chem.* 258:1235–1241, (1983)).

A potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease. Another obstacle to cloning restriction-modification systems lies in the discovery that some strains of *E.coli* react adversely to cytosine modification; they possess systems that destroy DNA containing methylated cytosine (Raleigh and Wilson, Proc. Natl. Acad. Sci., USA 83:9070–9074, (1986)). Cytosine-specific methylase genes cannot be cloned easily into these strains, either on their own, or together with their corresponding endonuclease genes. To avoid this problem it is necessary to use mutant strains of E.coli (McrA− and McrB−) in which these systems are defective.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

In accordance with the present invention there is provided a clone containing the genes for the Eag I restriction endonuclease and modification methylase derived from *Enterobacter agglomerans* (ATCC 53769), as well as related methods for the production of the enzymes. More specifically, this invention relates to clones which express the restriction endonuclease Eag I, an enzyme which recognizes the DNA sequence CGGCCG and cleaves after the first C. Eag I restriction endonuclease produced in accordance with the present invention is substantially pure and free of the contaminants normally found in Eag I preparations made by conventional techniques from *E.agglomerans*.

The preferred method for cloning this enzyme comprises forming a library containing the DNA from *E.agglomerans* (ATCC,53769), isolating those clones which contain DNA coding for the Eag I modification methylase by resistance to Not I endonuclease cleavage (GC GGCCGC) and screening among these to identify those that also contain the Eag I restriction endonuclease gene.

DETAILED DESCRIPTION OF THE INVENTION

The present invention relates to clones of the Eag I restriction and modification genes, as well to the restriction endonuclease Eag I produced from such clones. The Eag I genes are cloned by a method which takes advantage of the fact that certain clones which are selected on the basis of containing and expressing the Eag I modification methylase gene also contain the Eag I restriction gene. The DNA of such clones is resistant to digestion, in vitro, by the Not I and Eag I restriction endonucleases. The resistance to digestion by Not I, which recognizes a subset of Eag I sites (three out of four Eag I sites on pLSN3), allowed the use of a more active endonuclease; resulting in a greater probability of selectively isolating clones encoding the Eag I methylase and restriction endonuclease.

Figure 1:
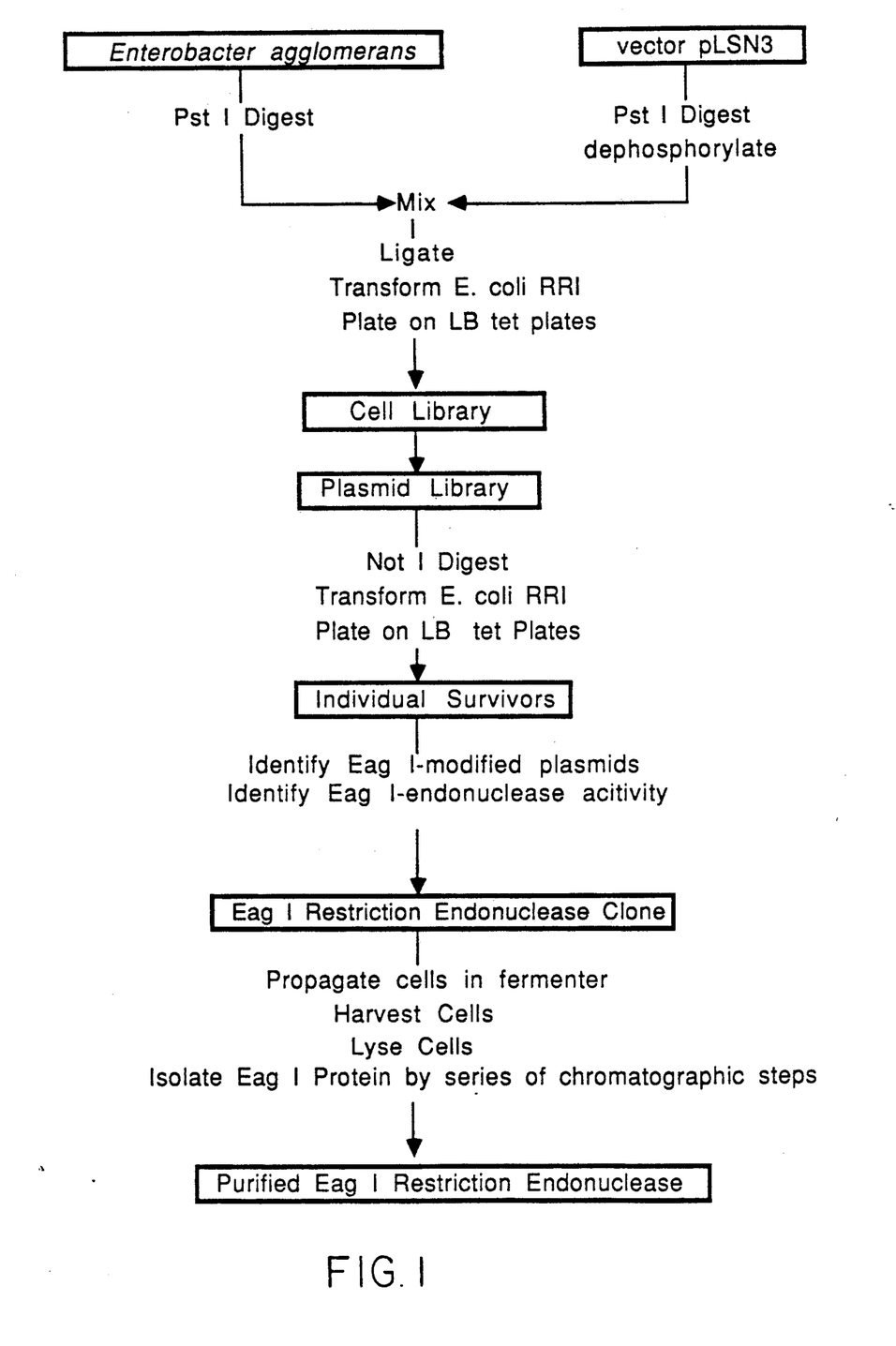
FIG. 1 illustrates the scheme for cloning and producing the Eag I restriction endonuclease.

The method described herein by which the Eag I restriction gene and methylase gene are preferably cloned and expressed are illustrated in FIG. 1, and they include the following steps:

1. The DNA of *Enterobacter agglomerans* is purified. Samples of this bacterium are available from: ATCC 53769.

2. The DNA is digested with a restriction endonuclease such as Pst I.

Figure 2:
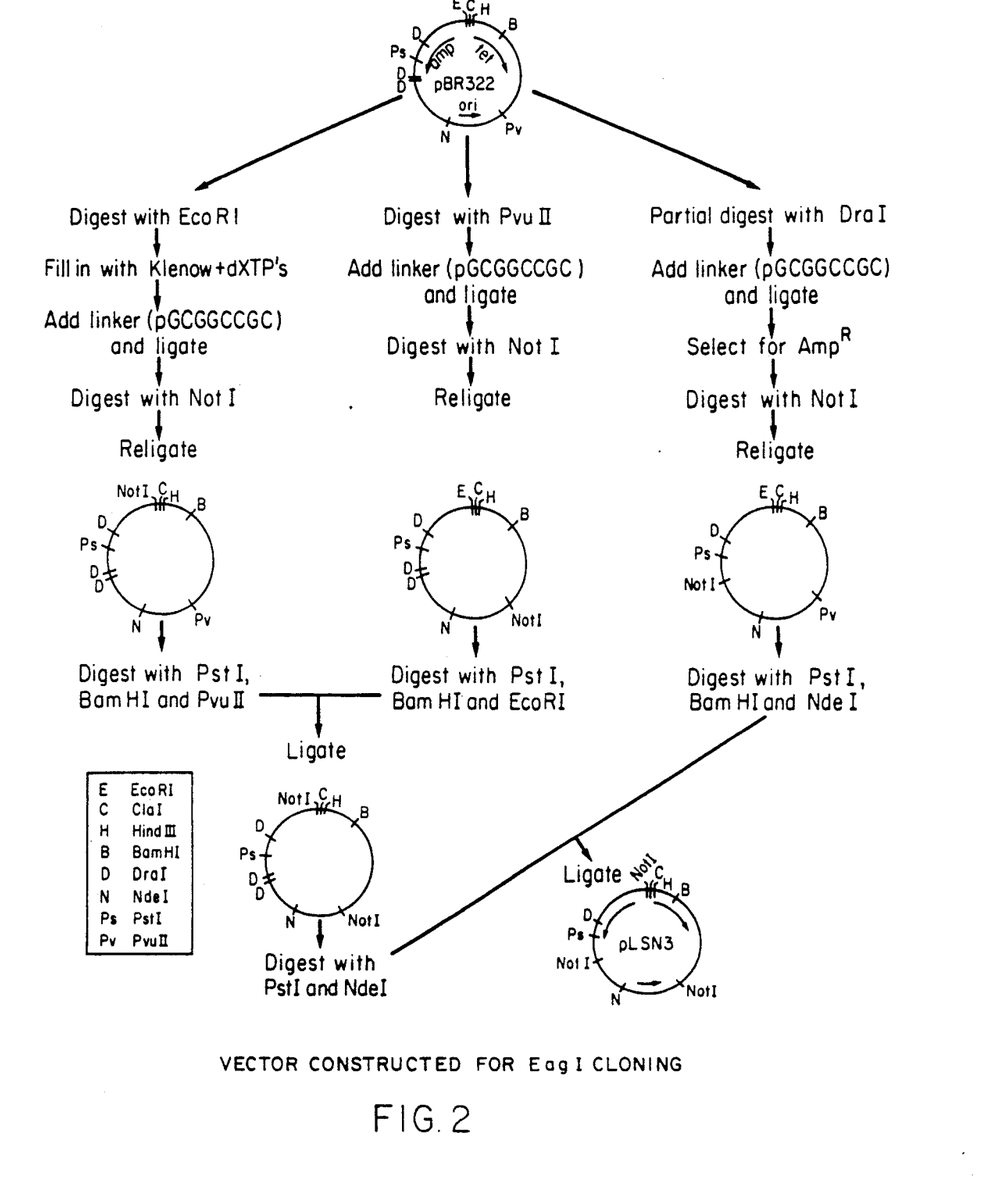
FIG. 2 is pLSN3, the vector used in cloning this system.
Figure 3A:
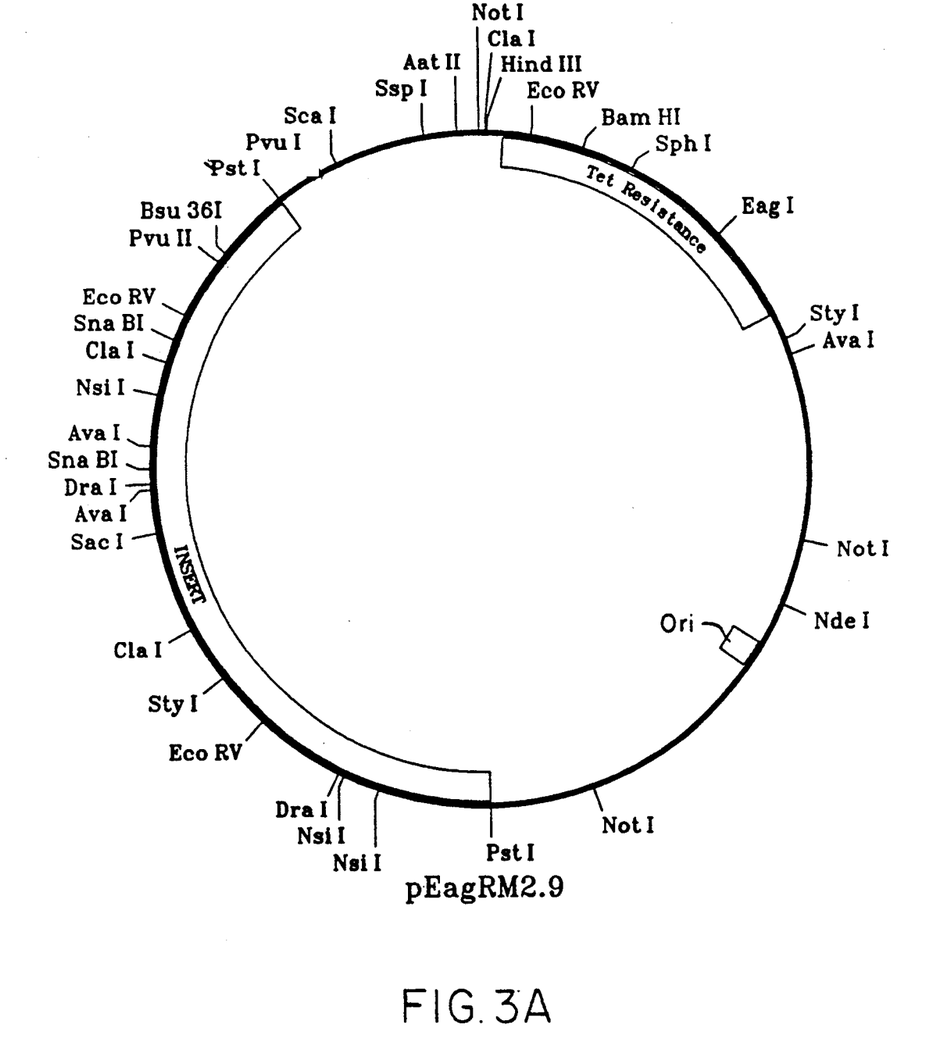
FIG. 3 is a restriction map of a 2.9 Kb Pst fragment of *E.agglomerans* DNA that encodes the Eag I restriction endonuclease and modification methylase. The fragment was cloned into the Pst I site of pLSN3 (see FIG. 2) to create pEagRM2.9, then it was transferred into the Pst I site of pUC19 (ATCC 37254) to create pEagRM2.9-19a and pEagRM2.9-19b. A mapping gel of pEagRM2.9-19b is also included.
Figure 3B:
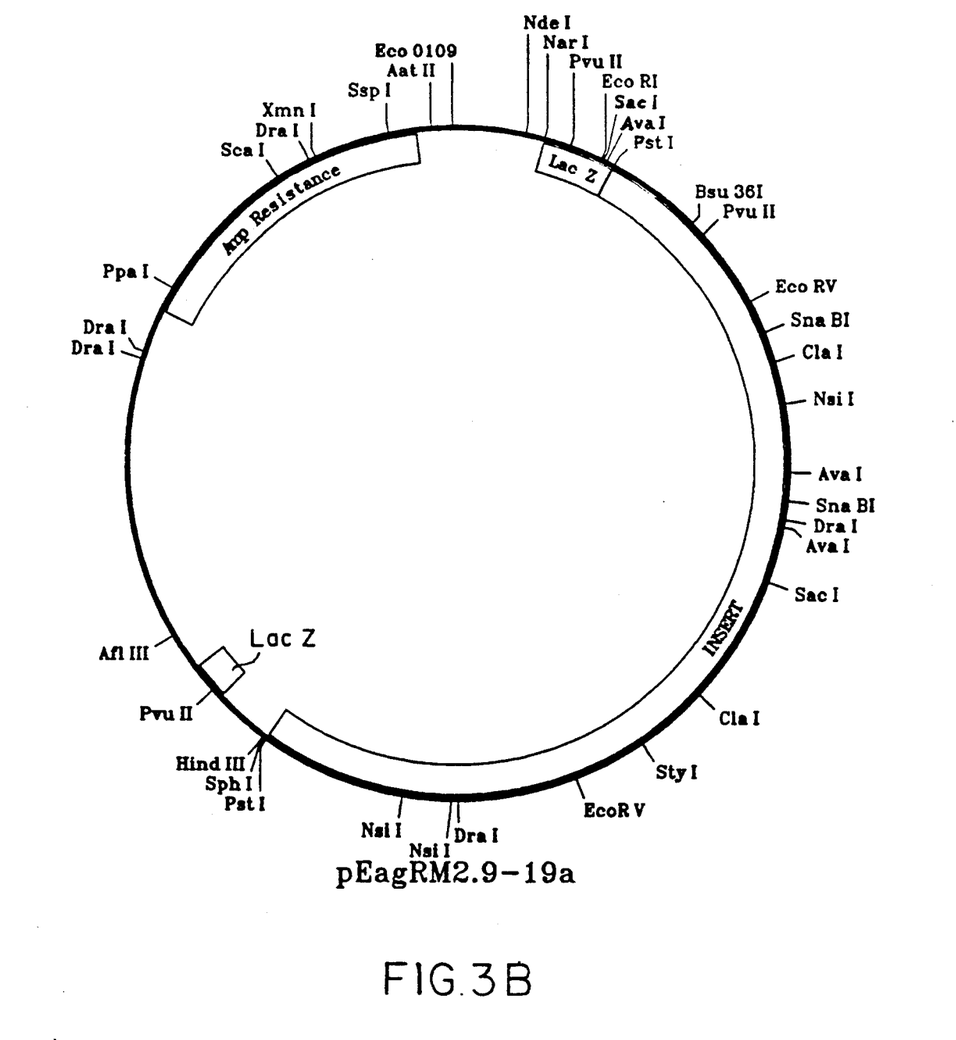
Figure 3C:
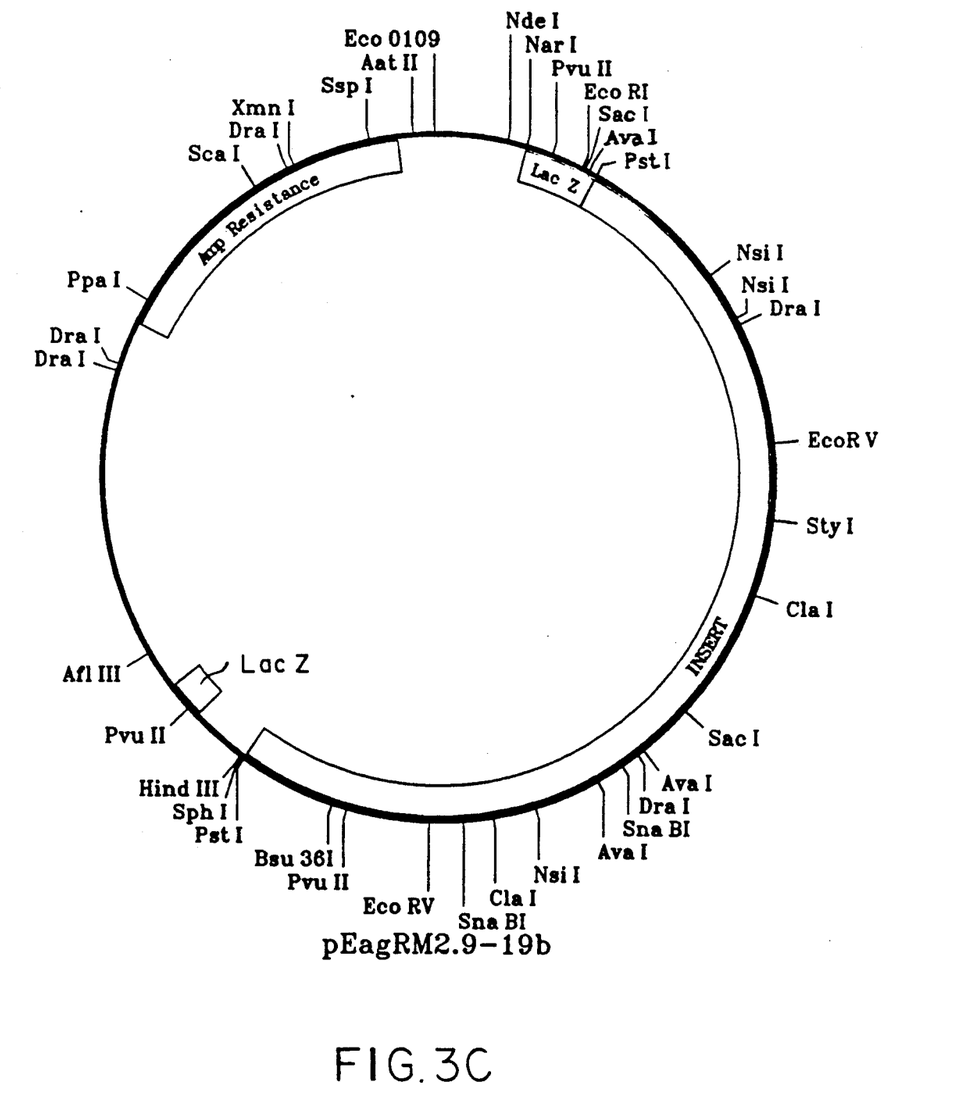
Figure 3D:
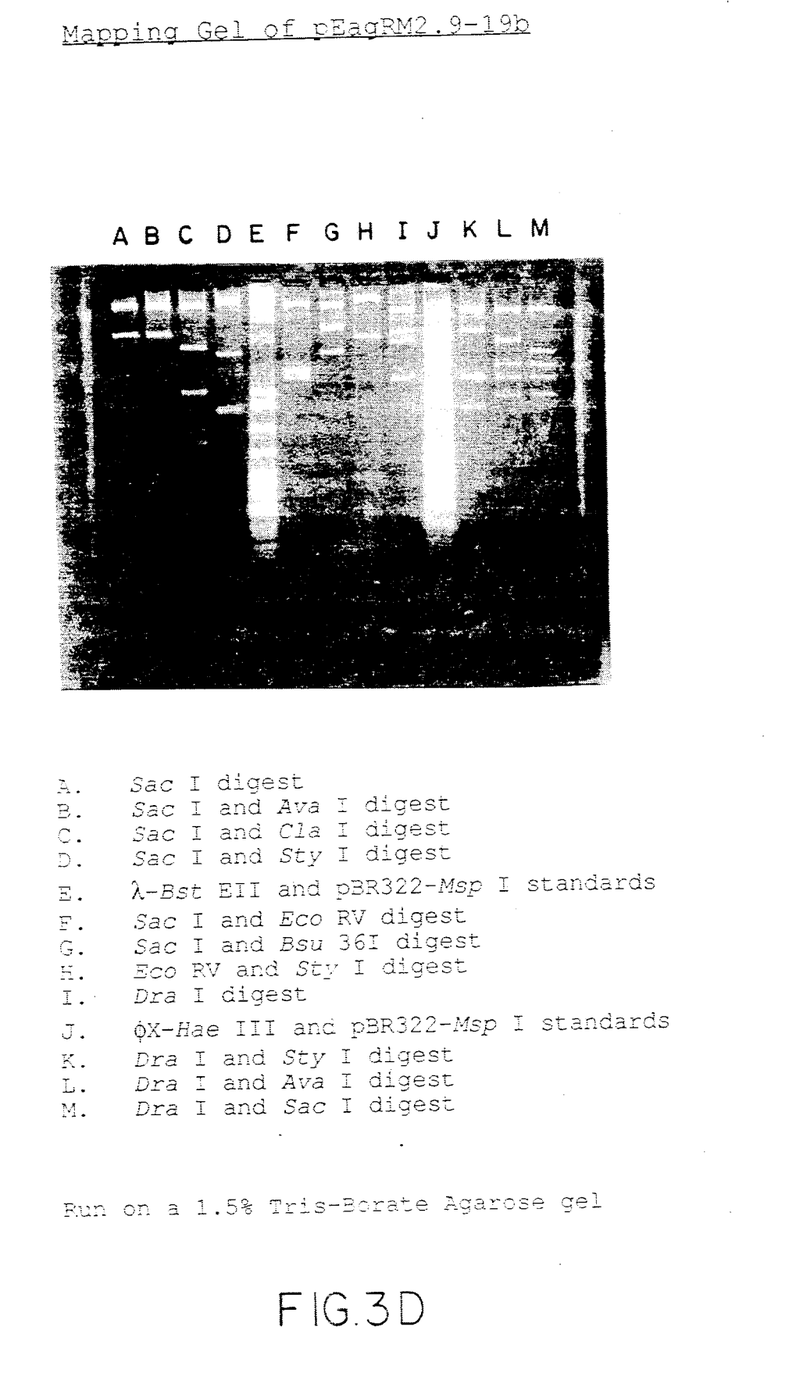

3. A vector containing four Eag I sites (three Not I sites) spread throughout the plasmid was constructed from pBR322 (ATCC 37017) (See FIG. 2).

4. The digested DNA is ligated to a cloning vector such as pLSN3, that contains one or more Eag I sites. The ligated DNA is transformed into an appropriate host such as *Escherichia coli* strain RR1 (ATCC 31343).

5. The transformed mixture is plated onto media selective for transformed cells, such as the antibiotic tetracycline. After incubation, the transformed colonies are collected together into a single culture, the cell library.

6. The recombinant plasmids are purified in toto from the cell library to make the plasmid library.

7. The plasmid library is digested to completion with the Not I restriction endonuclease, prepared from *Nocardia otitidis-caviarum* (ATCC 14630). Not I digestion differentially destroys unmodified, non-methylase-containing, clones, increasing the relative frequency of Eag I methylase clones.

8. The digested plasmid library is transformed back into an appropriate host such as *E.coli* RR1, and transformants are recovered by plating onto selective media. The colonies are picked and their DNA is analyzed for the presence of the Eag I modification gene: the plasmids that they carry are purified and incubated with the Eag I restriction endonuclease to determine whether they are resistant to digestion. Total cellular DNA (chromosomal and plasmid) is also purified and incubated with the Eag I restriction endonuclease. The DNA of clones that carry the Eag I modification gene should be fully modified, and both plasmid DNA and total DNA should be substantially resistant to digestion.

9. Clones carrying the Eag I restriction endonuclease are identified by preparing cell extracts of the Eag I methylase clones, identified in step 8, and assaying the extracts for Eag I restriction endonuclease activity.

10. The quantity of Eag I restriction endonuclease produced by the clones may be increased by elevating the gene dosage, through the use of high copy number vectors, and by elevating the transcription rate, through the use of highly active, exogenous promotors.

11. The Eag I restriction endonuclease may be produced from clones carrying the Eag I restriction and modification genes by propagation in a fermenter in a rich medium containing tetracycline. The cells are collected by centrifugation and disrupted by sonication to produce a crude cell extract containing the Eag I restriction endonuclease activity.

12. The crude cell extract containing the Eag I restriction endonuclease activity is purified by standard protein purification techniques such as affinity-chromatography and ion-exchange chromatography.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE

Cloning of Eag I Restriction Endonuclease Gene

1. DNA purification: Three grams of frozen *Enterobacter agglomerans* (ATCC 53769) cells were thawed on ice and resuspended in 25 ml of 0.1 M Tris-HCl pH 7.1; 0.1M EDTA. 60mg of lysozyme in 35ml of the above buffer was added. The suspension was incubated at 37° C. for 15 minutes. SDS was added from a 10% stock solution to adjust the final concentration of SDS to 1%. Proteinase K was added to a final concentration of 50µg/ml and the solution was incubated for one hour at 37° C. SDS and sarcosyl were added to the final concentrations of 3% each and incubated for 2 hours at 55° C. The DNA was dialyzed overnight into TE (10mM Tris-HCl pH.7.1; 1mM EDTA). The DNA was then diluted with an equal volume of TE. One gram/ml of CsCl and 100µg/ml of EtBr were added and the DNA was spun in a Ti70 rotor for 48 hours at 44,000rpm. The bands were removed and extracted with isopropanol saturated with water and CsCl. The DNA was then dialyzed overnight into TE and then phenol and chloroform extracted. This solution was dialyzed once again against TE overnight.

2. Digestion of DNA: 8 and 4 µg of *E.agglomerans* DNA were diluted into 200 and 100 µl of Pst I restriction endonuclease digestion buffer (10mM Tris pH 7.5, 10mM MgCl$_2$, 10mM mercaptoethanol, 100mM NaCl), respectively. 10 units of Pst I restriction endonuclease was added to the first tube containing 200µl. 100µl was then transfered from this tube to the second tube and both were incubated at 37° C. for 1 hr, then digestion was terminated by phenol extraction.

3. Ligation and transformation: 2 µg (40µl) of the combined Pst I digestions of *E.agglomerans* DNA was mixed with 0.5 µg (10 µl) of PstI-cleaved and dephosphorylated pLSN3 (FIG. 2). 75 µl of 4X ligation buffer (200mM Tris pH 7.5, 40mM MgCl$_2$, 80mM DTT, 4mM ATP), and 170 µl of sterile distilled water were added to bring the volume to 300 µl. 5 µl of T4 DNA ligase was added and the solution was incubated at 16° C. overnight. In each of five tubes, 24 µl of the ligation solution was mixed with 0.2 ml of ice-cold, competent *E.coli* RR1 (ATCC 31343) cells. The solution was incubated on ice for 25 minutes and then at 42° C. for 2 mins. Then 1.0 ml of Luria-broth (L-broth) was added and incubation was continued at 37° C. for 1 hr.

4. Cell Library: The transformed culture was gently centrifuged, 1.0 ml of the supernatant was discarded and the cells were resuspended in the remaining L-broth and spread onto Luria-agar (L-agar) plates containing 20 µg/ml tetracyline. The plates were incubated overnight at 37° C. The transformed cells that grew up on the surfaces of the plates were collected together by flooding each of the plates with 5 ml of L-broth, scraping the colonies together, and pooling the suspensions into a single tube.

5. Plasmid Library The cell library was centrifuged at 10K rpm for 5 minutes. The supernatant was discarded and the cell pellet was resuspended in 10 ml of ice-cold 10% sucrose, 50mM Tris-HCl (pH 8.0). 2 ml of lysozyme (10mg/ml in 0.25M Tris-HCl, pH8.0) and 8 ml of 0.25M EDTA were added. The solution was gently mixed and set on ice for 10 min. Then 4 ml of 10% SDS was added and the suspension was gently stirred; immediately following, 6 ml of 5M NaCl was added and mixed gently. The solution was placed on ice for 1 hour to induce cell lysis.

After cell lysis, the mixture was transferred to a 50 ml tube and centrifuged for 45 min. at 17K rpm, 4° C. The supernatant was extracted twice with phenol/CHCl$_3$ and once with CHCl$_3$. The DNA was then precipitated with two volumes of ethanol at −70° C. for 15 min. The DNA was spun at 15K rpm for 20 min at 4° C. The pellet was washed with 70% ethanol and then resuspended in 8 ml of TE (pH 8.0).

One g/ml of CsCl and 100µg/ml EtBr was added. The solution was transferred to a ⅝ in. ×3 in. centrifuge tubes and spun in a Beckman Ti70 rotor for 42 hours at 44K rpm, 17° C.

To collect the plasmids, the tubes were opened, illuminated with ultraviolet light, and the lower of the two fluorescent bands was collected by syringe. The DNA was diluted with two volumes of water and then precipitated with two volumes of ethanol in a dry ice-ethanol bath. The solution was spun for 20 minutes at 12K rpm, 0° C. The DNA was resuspended in 500 µl of TE and extracted with phenol and then CHCl$_3$. The DNA was reprecipitated with two volumes of ethanol and resuspended in 500 µl of TE. The plasmid DNA concentration was found to be approximately 100 µg/ml.

6. Digestion of the Plasmid Library: 2 µg (20 µl) of the plasmid library was diluted into 120 µl of Not I restriction endonuclease digestion buffer (10mM Tris pH 7.9, 10mM MgCl$_2$, 100µg/ml bovine serum albumin, 150mM NaCl, 0.01% Triton X-100). 60 units (6 µl) of Not I restriction endonuclease were added and the tube was incubated at 37° C. for 1 hr. Then another 60 units of Not I and 1 µl of Calf intestinal phosphotase was added and the reaction was incubated an additional 30 minutes at 37° C. The reaction was terminated by CHCl$_3$ extraction.

7. Transformation: 3, 6 and 12 µl (0.05, 0.1 and 0.2 µg) each of the digested library was mixed with 0.2 ml ice-cold competent *E.coli* RR1 (ATCC 31343) cells (section 3) and incubated on ice for 25 min. The mixture was warmed to 42° C. for 2 min. and then 1 ml of L-broth was added and incubated for 1 hour at 37° C. The suspension was briefly microfuged and 1 ml was removed. The cell pellet was resuspended in the remaining L-broth and plated onto an L-agar containing 20 µg/ml tetracycline. The plate was incubated overnight at 37° C. Not I digestion reduced the number of transformants 10$^3$-fold compared with transformation by undigested plasmids. A total of thirteen colonies survived on the three plates. Five ml of L-broth containing tetracycline was inoculated with each of the survivors to prepare a miniculture, and streaked onto an L-agar plate containing tetracycline, to prepare a master stock.

8. Analysis of surviving individuals: The thirteen 5 ml cultures of the surviving colonies obtained from section 7 were minipreped to isolate the plasmids that they carried by the purification procedure adapted from the method of Maniatis, T., Fritsch, E. F. and Sambrook, J. (1982) Molecular Cloning. A Laboratory Manual. Cold Spring Harbor Laboratories, New York; pages 368–369.

Miniprep Procedure

Each 5 ml culture was centrifuged at 5K rpm for 5 minutes; the supernatant was discarded and the cell pellet was resuspended in 0.1 ml of 25mM Tris-HCl,pH 8.0, 10mM EDTA, 50mM glucose, containing 4 mg/ml lysozyme. The solution was transfered to a 1.5 ml Eppendorf tube. After 5 minutes at room temperature, 0.2 ml of 0.2N NaOH, 1% SDS was added to each tube and the tubes were immediately inverted gently to lyse the cells, then placed on ice for 5 minutes. Then 0.15 ml of 3M/5M potassium acetate, pH 4.8, was added to each, vortexed for 10 seconds and incubated on ice for 5 minutes. The precipitates that formed were spun down in an Eppendorf centrifuge at 4° C. for 5 minutes. Each supernatant was transfered to a new Eppendorf tube containing 1 ml of ethanol and mixed. After 2 minutes at room temperature, the tubes were spun for 2 minutes at room temp. to pellet the precipitated nucleic acids. The supernatants were discarded and the pellets were rinsed with 1 ml of 70% ethanol and then air-dried at room temperature for 5 minutes. The pellets were resuspended in 50 μl of 10mM Tris, 1mM EDTA, pH 8.0 containing DNase-free pancreatic RNase (20 μg/ml). The plasmid minipreps were subsequently analyzed by digestion with Eag I, Not I and Pst I.

9. Eag I Methylase Gene Clones: Twelve of the 13 plasmids that were analyzed were found to be resistant to Eag I and Not I digestion and to carry a 2.9 Kb Pst I fragment of E.agglomerans DNA.. One of the 12 resistant plasmids contained an additional 0.9 Kb Pst I fragment of E.agglomerans DNA. The presence of the additional fragment did not affect the properties of the plasmid, so for simplicity only plasmids carrying the 2.9 Kb fragment were analyzed in detail (FIG. 3). These plasmids, typical of which is pEagRM2.9, were shown to encode not only the Eag I modification methylase but also the Eag I restriction endonuclease. A sample of plasmid pEagRM2.9 has been deposited at the American Type Culture Collection under ATCC Accession No. 40853.

10. Eag I Restriction Gene Clone: pEggRM2.9, and similar plasmids, were found to encode and express the Eag I restriction endonuclease by assaying extracts of E.coli RR1 that carried the plasmids.

Endonuclease Assay

A 1 liter culture of the cells to be assayed was grown overnight at 37° C. in L-broth containing 20 μg/ml tetracycline. The culture was centrifuged at 10K rpm for 5 min and the cell pellet (~7 grams) was resuspended in 20 ml of 10mM KPO$_4$ pH 7.5, 0.1M NaCl, 0.1mM EDTA. 1 ml of 10 mg/ml lysozyme and 2 ml of 0.1M EDTA was added and the suspension was left on ice for 15 minutes. The suspension was sonicated gently for four 20-second bursts to disrupt the cells. 0.2 ml of 5M NaCl was added to the sonicated extract and the cell debris was then removed by centrifugation for 10 minutes at 12K rpm. The supernatant was assayed for endonuclease activity in the following way:

14 μg (28 μl) of Bam HI-linearized pLSN3 was diluted into 700 μl of Eag I restriction endonuclease digestion buffer (150mM NaCl, 10mM Tris-HCl,pH 8.0, 10mM MgCl2, 10mM 2-mercaptoethanol, 100μg/ml BSA). The solution was dispensed into 6 tubes, 200 μl into the first tube and 100 μl into each of the remaining 5 tubes. 1 μl of the extract was added to the first tube to achieve 0.25 μl extract/μg DNA. 100 μl was then removed from the first tube and transferred to the second tube to achieve 0.125 μl/μg. 100μl serial transfers were continued into tubes 3 (0.06 μl/μg), 4 (0.03 μl/μg) and 5 (0.015 μl/μg). The sixth tube received no extract and served as a negative control. The tubes were incubated at 37° C. for 30 minutes, then 20 μl from each was analyzed by gel electrophoresis. The extract was found to contain approximately 3×10$^4$ units of Eag I restriction endonuclease per ml, which corresponds to about 1×10$^5$ units per gram of cells.

11. Phage-resistance of the Eag I RM clones: Some restriction-modification systems express the restriction phenotype when they are cloned into E.coli, and some do not. The restriction phenotype is the ability of cells to survive infection by phages and the inability of phages to reproduce. E.coli RR1 carrying pEagRM2.9, or other plasmids containing the 2.9 Kb Pst I fragment, displays a restriction phenotype. Lambdoid phages plaque with an efficiency of approximately 10$^{-2}$ on these clones compared to an efficiency of 1 on the same strain carrying pLSN3.

12. Transfer of the 2.9 Kb fragment to pUC19: 32 μg (100 μl) of purified pEagRM2.9 DNA was prepared in 800 μl of Pst I restriction endonuclease digestion buffer (section 2). 300 units of Pst I restriction endonucleases was added and the solution was incubated at 37° C. for 90 minutes. The digestion mix was run out on a 0.7% Tris-Acetate agarose gel (140 μl/well). The desired 2.9 Kb Pst I E.agglomerans fragment ran sufficiently below the 4.3 Kb band of the vector and was easily cut out of the gel.

To extract the 2.9 Kb fragment from the agarose, it was first frozen at −70° C. and then thawed. An equal volume of running buffer was added and then the mixture was extruded through an 18-guage needle and refrozen. The thawed mixture was extruded again, diluted to 11 ml total volume and spun in a Ti70 rotor at 55K rpm for 1 hour.

The supernatant was brought to 0.1M NaCl and precipitated with two volumes of ethanol. The DNA pellet was resuspended in TE (10mM Tris-HCl, pH8.0, 10mM EDTA) and then extracted with phenol, phenol/CHCl$_3$ and finally CHCl$_3$. The DNA was reprecipitated; rinsed with 70% ethanol; and resuspended in 60 μl TE.

0.5 μg (5 μl) of the gel purified 2.9 Kb Pst I fragment was mixed with 0.1 μg of Pst I-cleaved and dephosphorylated pUC19. 15 μl of 4X ligation buffer (section 3) and 38 μl of sterile distilled water were added to bring the volume to 60 μl. 1 μl of T4 DNA ligase was added and the solution was incubated at 16° C. for 2 hr. The ligation was sterilized by extraction with 60 μl of chloroform, then clarified by brief microcentrifugation. 1, 5 and 10 μl of the sterile ligation was mixed with 200 μl of competent, ice-cold, E.coli RR1 and incubated on ice for 25 minutes and then heat shocked at 42° C. for 2 min. 1 ml of L-broth was then added to each mixture and incubated at 37° C. for 1 hour. The cells were pelleted and 1 ml of supernatant was removed. The cells were then resuspended in the remaining L-broth and then plated onto L-agar plates containing 100 μg/ml ampicillin and transformants were recovered after incubation at 37° C., overnight.

Figure 4:
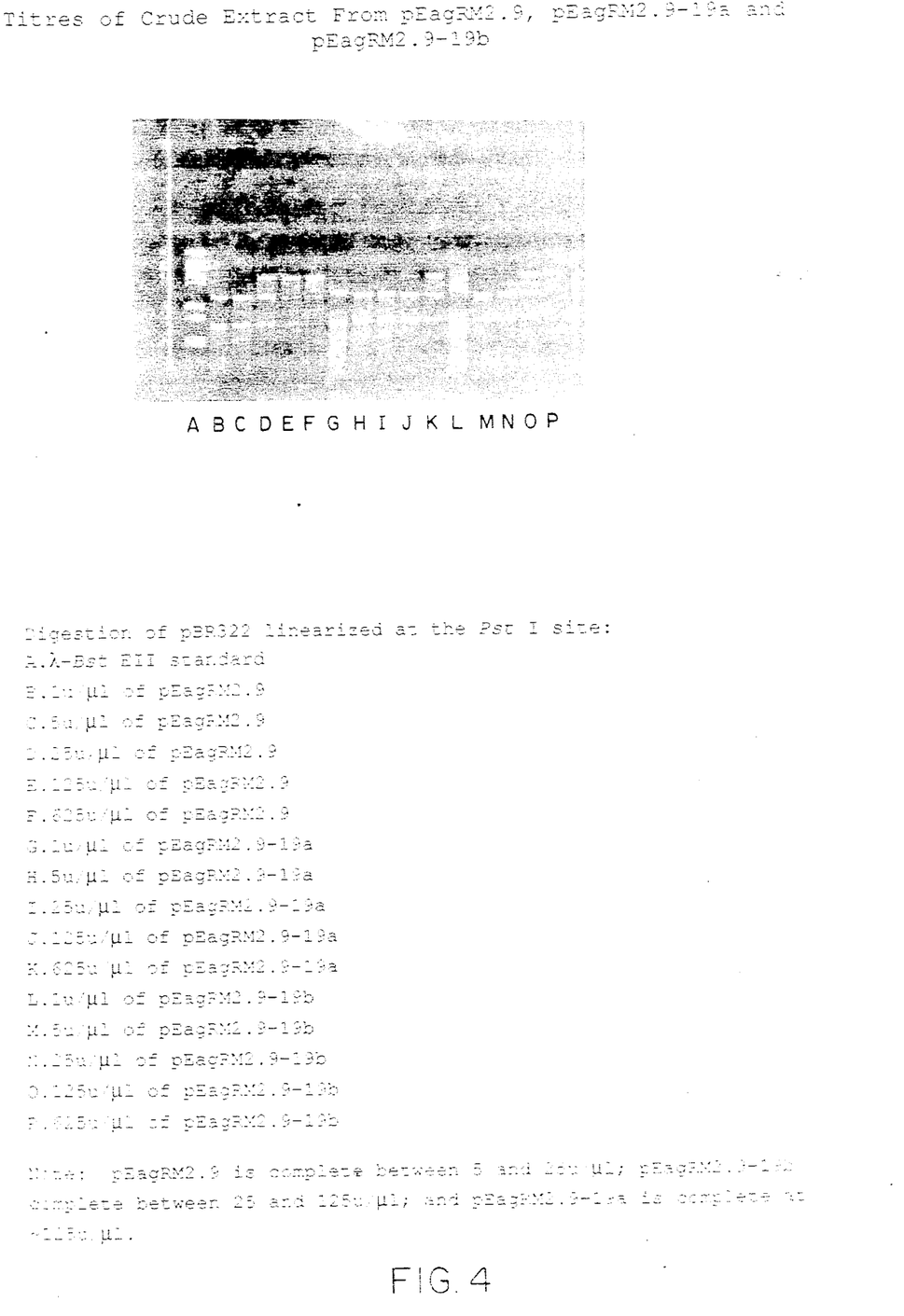
FIG. 4 is a photograph of an agarose gel demonstrating Eag I restriction endonuclease activity in cell extracts of *E.coli* RR1 (ATCC 31343) carrying pEagRM2.9, pEagRM2.9-19a and pEagRM2.9-19b.

8 transformant colonies were picked and screened by the miniprep procedure (section 8) to identify plasmids composed of pUC19 with the 2.9 Kb fragment inserted at the Pst I site. All plasmids were found to contain the 2.9 Kb fragment; 2 contain the 2.9 Kb fragment in one orientation (pEagRM2.9-19a) and the other 6 were in the opposite orientations (pEagRM2 9-19b). All exhibit complete resistance to Eag I digestion. A crude cell extract of *E.coli* RR1 carrying each of these plasmids was assayed for Eag I restriction endonuclease activity (FIG. 4).

The extracts from pEagRM2.9-19b were found to contain approximately 5-fold more Eag I restriction endonuclease than the parental clone and extracts from pEagRM2.9-19a contain ~10-fold more endonuclease, ~1×10⁶ units/gm cells.

*E.coli* RR1 carrying pEagRM2.9-19a is the preferred host from which the Eag I restriction endonuclease can be purified. The strain should be grown to stationary phase at 37° C. in a fermenter, in L-broth containing ampicillin. The cells should then be collected by centrifugation and either broken immediately for extract preparation, or stored frozen at −70° C. until it is convenient to do so.

What is claimed is:

1. Isolated DNA coding for the EagI restriction endonuclease, wherein the isolated DNA is obtainable from the vector pEagRM2.9.

2. A recombinant DNA vector comprising a vector into which a DNA segment coding for the EagI endonuclease produced from E. agglomerans ATCC No. 53769 has been inserted.

3. Isolated DNA coding for the EagI restriction endonuclease and methylase, wherein the isolated DNA is obtainable from the vector pEagRM2.9.

4. A cloning vector which comprises the isolated DNA of claim 1.

5. A cloning vector which comprises the isolated DNA of claim 3.

6. The cloning vector of claim 5, wherein the cloning vector comprises pEagRM2.9.

7. A host cell transformed by the vector of claim 5 or 6.

8. A method of producing EagI restriction endonuclease comprising culturing a host cell transformed with the vector of claim 4, 5 or 6 under conditions suitable for the expression of said endonuclease.

9. A method of cloning DNA coding for an EagI restriction endonuclease comprising:

(a) purifying DNA from E. agglomerans ATCC No. 53769;
   (b) digesting the purified DNA with PstI to form DNA fragments;
   (c) ligating the DNA fragments into cloning vector pLSN3;
   (d) transforming a host cell with the cloning vector of step (c) to form a cell library;
   (e) purifying recombinant vectors from the cell library to form a plasmid library;
   (f) contacting the plasmid library of step (e) with NotI to form a digestion pool, transforming the digestion pool into a host cell, and screening for the presence of one or more cloning vectors containing DNA coding for an EagI methylase;
   (g) screening the cloning vectors of step (f) which contain DNA coding for EagI methylase for the presence of DNA coding for an EagI restriction endonuclease; and
   (h) isolating the cloning vectors of step (g) which contain DNA coding for EagI restriction endonuclease.

10. A method of producing EagI restriction endonuclease comprising:

(a) purifying DNA from E. agglomerans ATCC No. 53769;
   (b) digesting the purified DNA with PstI to form DNA fragments;
   (c) ligating the DNA fragments into cloning vector pLSN3;
   (d) transforming a host cell with the cloning vector of step (c) to form a cell library;
   (e) purifying recombinant vectors from the cell library to form a plasmid library;
   (f) contacting the plasmid library of step (e) with NotI to form a digestion pool, transforming the digestion pool into a host cell, and screening for the presence of one or more cloning vectors containing DNA coding for an EagI methylase;
   (g) screening the cloning vectors of step (F) which contain DNA coding for EagI methylase for the presence of DNA coding for an EagI restriction endonuclease;
   (h) isolating the cloning vectors of step (g) which contain DNA coding for EagI restriction endonuclease; and
   (i) culturing a host cell transformed with the cloning vector of step (h) under conditions suitable for expression of EagI restriction endonuclease.

* * * * *